United States Patent
Cross, Jr. et al.

(10) Patent No.: US 8,119,848 B2
(45) Date of Patent: Feb. 21, 2012

(54) PREPARATION OF ALKYLATION FEED

(75) Inventors: William M. Cross, Jr., Seabrook, TX (US); Lawrence A. Smith, Jr., Pasadena, TX (US); Gary G. Podrebarac, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 675 days.

(21) Appl. No.: 12/243,459

(22) Filed: Oct. 1, 2008

(65) Prior Publication Data

US 2010/0081854 A1    Apr. 1, 2010

(51) Int. Cl.
*C07C 2/06* (2006.01)
*C07C 2/56* (2006.01)

(52) U.S. Cl. ......... 585/323; 585/332; 585/518; 585/448

(58) Field of Classification Search .................. 585/323, 585/332, 518, 448
See application file for complete search history.

(56) References Cited

U.S. PATENT DOCUMENTS

| | | | |
|---|---|---|---|
| 2,762,856 A | 9/1956 | Jones et al. | |
| 2,859,260 A | 11/1958 | Stiles | |
| 3,013,092 A | 12/1961 | Watson et al. | |
| 4,313,016 A | 1/1982 | Manning | |
| 4,540,839 A | 9/1985 | Keyworth et al. | |
| 5,003,124 A | 3/1991 | Smith, Jr. et al. | |
| 5,026,933 A * | 6/1991 | Blain et al. ........................ | 585/7 |
| 5,300,126 A | 4/1994 | Brown et al. | |
| 6,335,473 B1 | 1/2002 | Bakshi et al. | |
| 6,440,299 B2 * | 8/2002 | Hearn et al. ................... | 208/189 |
| 6,774,275 B2 | 8/2004 | Smith, Jr. et al. | |
| 6,858,770 B2 | 2/2005 | Smith, Jr. et al. | |
| 6,995,296 B2 | 2/2006 | Smith, Jr. et al. | |
| 7,145,049 B2 * | 12/2006 | Loescher et al. ............... | 585/533 |
| 2005/0143612 A1 | 6/2005 | Hwang et al. | |

FOREIGN PATENT DOCUMENTS

EP    0432447 A1 *    6/1991

OTHER PUBLICATIONS

International Search Report and Written Opinion issued Apr. 14, 2010 in corresponding International application No. PCT/US2009/056011 (12 pages).

* cited by examiner

*Primary Examiner* — Thuan Dinh Dang
(74) *Attorney, Agent, or Firm* — Osha • Liang LLP

(57) ABSTRACT

A process for treating an alkylation feedstock comprising olefins, n-alkanes, iso-alkanes, and impurities including one or more of butadiene, oxygenates, nitrogen-containing compounds, and sulfur-containing compounds, the process including: contacting an alkylation feedstock containing at least one of oxygenates and nitrogen-containing compounds with water to produce a hydrocarbon fraction having a reduced concentration of the at least one of oxygenates and nitrogen-containing compounds and an aqueous fraction comprising at least a portion of the at least one of oxygenates and nitrogen-containing compounds; separating water from the hydrocarbon fraction having a reduced concentration to produce a hydrocarbon fraction having a reduced water content; contacting the hydrocarbon fraction having a reduced water content with an oligomerization catalyst in a first oligomerization reaction zone under oligomerization conditions to react at least a portion of the olefins to form a reactor effluent comprising olefin oligomers; and feeding at least a portion of the reactor effluent to an alkylation unit.

17 Claims, 3 Drawing Sheets

PREPARATION OF ALKYLATION FEED

BACKGROUND OF DISCLOSURE

1. Field of the Disclosure

Embodiments disclosed herein relate generally to the alkylation of paraffinic hydrocarbon feedstocks. More particularly, embodiments disclosed herein relate to a process for the preparation of an olefin-containing feed and an alkylation process using the prepared feed.

2. Background

Alkylation is the reaction of paraffins, usually isoparaffins, with an olefin in the presence of a strong acid which produces paraffins, e.g., of higher octane number than the starting materials and which boils in the range of gasolines. In petroleum refining, the alkylation reaction is generally the reaction of a $C_3$ to $C_5$ olefin with isobutane.

In refining alkylations, hydrofluoric or sulfuric acid catalysts are commonly used. For sulfuric acid catalyzed alkylation, low temperature or cold acid processes are favored, minimizing side reactions. In a typical process, the reaction is carried out in a reactor where the hydrocarbon reactants are dispersed into a continuous acid phase.

For example, U.S. Pat. No. 2,762,853 discloses an alkylation process including feeding isoparaffins, such as isobutane or isopentane and $C_2$-$C_5$ monoolefins to an alkylation reactor. The alkylation reaction is catalyzed with sulfuric acid in excess of 88 percent, preferably in excess of 96 percent. The alkylation products are then separated into gasoline range components and heavier alkylate products.

As another example, U.S. Pat. No. 2,859,260 discloses an alkylation process including reacting isoparaffins with olefins in the presence of a sulfuric acid catalyst. The reaction product is then separated to recover a hydrocarbon-rich phase and an acid-rich phase. The hydrocarbon-rich phase is further treated to remove catalyst esters from the hydrocarbon phase, among other downstream operations. Another example of a prior art alkylation process is disclosed in U.S. Pat. No. 3,013,092.

Alkylation feedstocks, such as a fluid catalytic cracking (FCC) $C_4$ cut may include numerous components, including n-butane, isobutane, n-butene, and isobutene. Undesired components in alkylation feeds may include oxygenates (such as water and oxygenated hydrocarbons, such as ethers and alcohols), dienes (such as butadiene), nitrogen-containing compounds (such as nitrites and amines), and sulfur-containing compounds (such as methyl mercaptan and ethyl mercaptan). The presence of these undesired compounds may result in increased acid consumption in both hydrofluoric acid (HF) and sulfuric acid ($H_2SO_4$) alkylation units.

Accordingly, there exists a need for processes to improve the performance of alkylation units, including decreased acid consumption.

SUMMARY OF THE DISCLOSURE

In one aspect, embodiments disclosed herein relate to a process for treating an alkylation feedstock comprising olefins, n-alkanes, iso-alkanes, and impurities including one or more of butadiene, oxygenates, nitrogen-containing compounds, and sulfur-containing compounds, the process including: contacting an alkylation feedstock containing at least one of oxygenates and nitrogen-containing compounds with water to produce a hydrocarbon fraction having a reduced concentration of the at least one of oxygenates and nitrogen-containing compounds and an aqueous fraction comprising at least a portion of the at least one of oxygenates and nitrogen-containing compounds; separating water from the hydrocarbon fraction having a reduced concentration to produce a hydrocarbon fraction having a reduced water content; contacting the hydrocarbon fraction having a reduced water content with an oligomerization catalyst in a first oligomerization reaction zone under oligomerization conditions to react at least a portion of the olefins to form a reactor effluent comprising olefin oligomers; and feeding at least a portion of the reactor effluent to an alkylation unit.

In another aspect, embodiments disclosed herein relate to a process for treating an alkylation feedstock including olefins, n-alkanes, iso-alkanes, and impurities including one or more of butadiene, oxygenates, nitrogen-containing compounds, and sulfur-containing compounds, the process including: contacting the alkylation feedstock with water to produce a hydrocarbon fraction having a reduced concentration of at least one of nitrogen-containing compounds and oxygenates and an aqueous fraction comprising at least a portion of at least one of the nitrogen-containing compounds and the oxygenates; feeding hydrogen and the hydrocarbon fraction having a reduced concentration to a catalytic distillation reactor system comprising at least one reaction zone containing a hydrogenation catalyst formed as a distillation structure; concurrently in the distillation column reactor system: i) contacting the hydrogen and the dienes with the hydrogenation catalyst thereby catalytically reacting at least a portion of the dienes and hydrogen to form olefins; and ii) fractionating the hydrocarbons from the water; recovering the water and unreacted hydrogen as an overheads fraction; recovering a hydrocarbon fraction having a reduced dienes concentration as a bottoms fraction; contacting the hydrocarbon fraction having a reduced diene content with an oligomerization catalyst in a first oligomerization reaction zone under oligomerization conditions to react at least a portion of the olefins to form a reactor effluent comprising olefin oligomers; and feeding at least a portion of the reactor effluent to an alkylation unit.

In another aspect, embodiments disclosed herein relate to a process for treating an alkylation feedstock comprising olefins, n-alkanes, iso-alkanes, and impurities including one or more of butadiene, oxygenates, nitrogen-containing compounds, and sulfur-containing compounds, the process including: contacting the alkylation feedstock with water to produce a hydrocarbon fraction having a reduced concentration of at least one of nitrogen-containing compounds and oxygenates and an aqueous fraction comprising at least a portion of the nitrogen-containing compounds and the oxygenates; feeding hydrogen and the hydrocarbon fraction having a reduced concentration to a catalytic distillation reactor system comprising at least one reaction zone containing a catalyst formed as a distillation structure; concurrently in the distillation column reactor system: i) contacting the hydrogen and the dienes with the catalyst thereby catalytically reacting at least a portion of the dienes and hydrogen to form the corresponding olefins; and ii) contacting dienes and mercaptans with the catalyst thereby catalytically reacting at least a portion of the dienes and mercaptans to form heavy sulfides; iii) fractionating the resulting hydrocarbons from the water; recovering the water and unreacted hydrogen as an overheads fraction; recovering a hydrocarbon fraction comprising the heavy sulfides and other sulfur-containing compounds as a bottoms fraction; and recovering a hydrocarbon fraction comprising $C_4$ olefins as a side draw; contacting the side draw with an oligomerization catalyst in a first oligomerization reaction zone under oligomerization conditions to react at least a portion of the olefins to form a reactor effluent comprising olefin oligomers; and feeding at least a portion of the reactor effluent to an alkylation unit.

Other aspects and advantages will be apparent from the following description and the appended claims.

DETAILED DESCRIPTION

Figure 1:
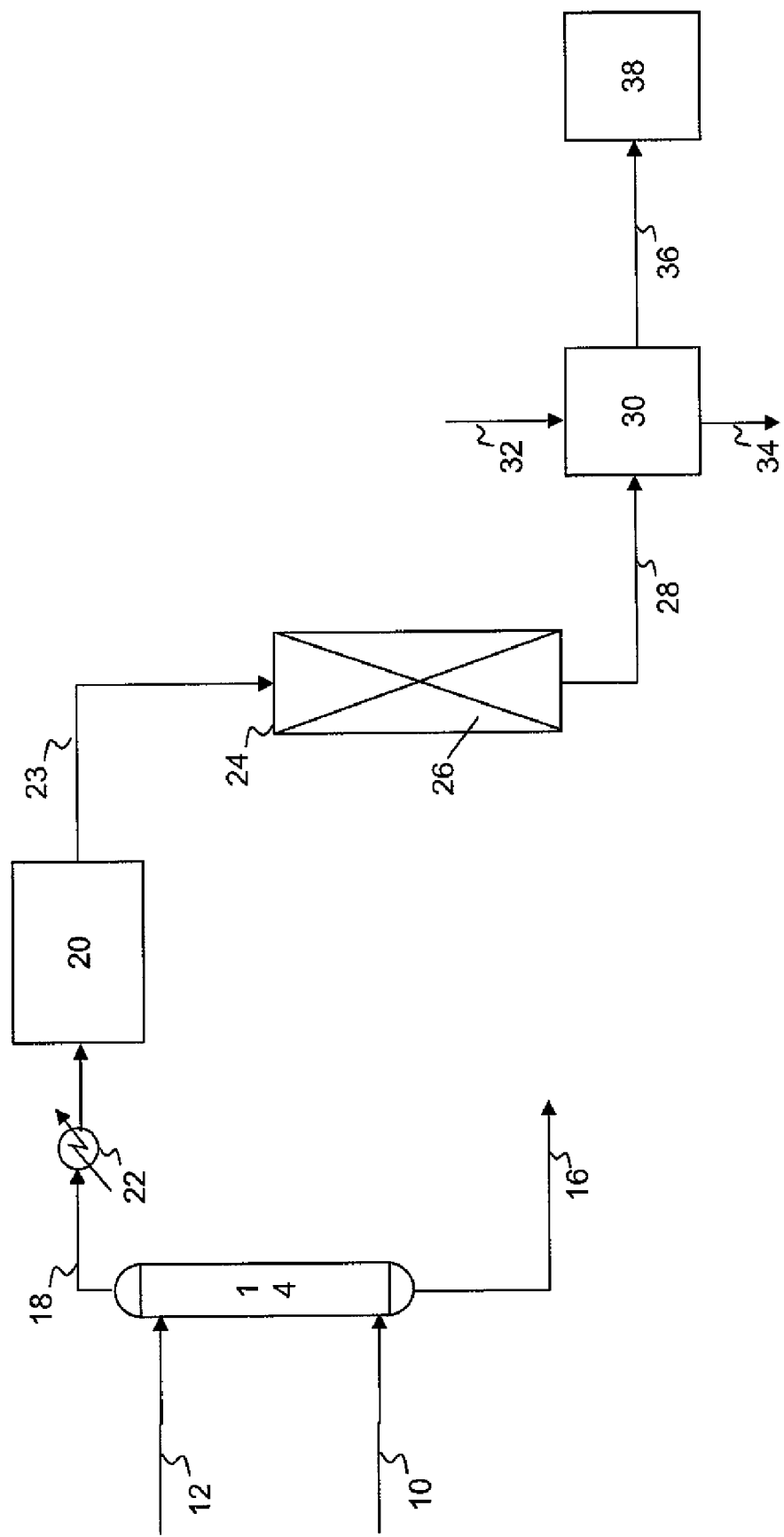
FIG. 1 is a simplified process flow diagram of a process for treating alkylation feedstocks according to embodiments disclosed herein.

In one aspect, embodiments disclosed herein relate to the alkylation of hydrocarbon feedstocks. More particularly, embodiments disclosed herein relate to a process for the preparation of an olefin-containing feedstocks and an alkylation process using the prepared feed. In particular, embodiments disclosed herein relate to processes that may decrease the acid consumption in an alkylation process.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Alkylation feedstocks used in embodiments disclosed herein may include mixtures of various olefins and paraffins. For example, alkylation feedstocks may include $C_1$-$C_5$ paraffins, including n-alkanes and iso-alkanes, and $C_2$-$C_5$ olefins. Olefins may include n-olefins (straight chain olefins), iso-olefins (branched olefins), and mixtures thereof. In some embodiments, alkylation feedstocks may include a $C_3$-$C_5$ light cracked naphtha (LCN) cut.

In certain embodiments, paraffins may include $C_4$ alkanes (n-butane and isobutane), $C_5$ alkanes (n-pentane, neopentane, and isopentane), and mixtures thereof. In other embodiments, olefins may include ethylene, propylene, $C_4$ olefins (such as 1-butene, 2-butene, isobutylene, or mixtures thereof), $C_5$ olefins (such as 1-pentene, 2-pentene, isopentenes, and mixtures thereof), and mixtures thereof.

Alkylation feedstocks, such as a $C_4$-$C_6$ light cracked naphtha cut, may also include oxygenates, such as water and alcohols, mercaptans and other sulfur-containing compounds, nitrogen-containing compounds, such as nitriles and amines, and dienes, such as butadiene. Each of these may consume acid, such as hydrofluoric acid or sulfuric acid, when fed to an acid alkylation unit. Treatment of alkylation feedstocks according to embodiments disclosed herein may prevent acid-consuming components from entering the alkylation unit.

In some embodiments, it may be desired to oligomerize a portion of the alkylation feedstock prior to alkylation. For example, U.S. Pat. Nos. 6,774,275, 6,858,770, and 6,995,296, each of which is incorporated herein by reference, disclose the impact in reducing cooling requirements in alkylation units by feeding $C_4$ olefin oligomers (dimers and trimers) to the alkylation unit. Nitrogen-containing compounds, sulfur-containing compounds, dienes, oxygenates, and other components in an alkylation feedstock may also have a detrimental impact on the oligomerization process, poisoning the alkylation catalyst and/or resulting in undesired polymerization. Treatment of alkylation feedstocks according to embodiments disclosed herein may additionally improve oligomerization catalyst performance.

Treatment of the hydrocarbon feedstock may include various steps to remove undesired compounds from the alkylation feed. For example, in some embodiments, oxygenates and/or nitrogen-containing compounds may be removed by contacting the hydrocarbon feedstock with water, such as by water-washing. Entrained water in the water-washed hydrocarbon fraction, having a reduced concentration of oxygenates and/or nitrogen-containing compounds may then be removed, such as by distillation or adsorption. In some embodiments, such as where the water is removed via distillation, the distillation structure may include a catalyst for reacting a) dienes and hydrogen to form olefins, b) dienes and mercaptans to form heavy sulfides, or c) combinations of a) and b). The treated feed, having a reduced nitrile, oxygenate, diene, and/or sulfur content, may then be fed to an oligomerization unit to oligomerize at least a portion of the olefins, and the resulting oligomerization unit effluent may then be reacted with sulfuric acid or hydrofluoric acid to produce an alkylate product.

Treatment of alkylation feedstocks according to embodiments disclosed herein, may effectively reduce or eliminate one or more of oxygenates, nitrogen-containing compounds, dienes and sulfur-containing compounds in the resulting treated feed to be fed to an alkylation unit. In some embodiments, the treated alkylation feed recovered via processes disclosed herein may include 0.1 percent or less dienes; 500 ppm or less in other embodiments; and 100 ppm or less in yet other embodiments, each on a weight basis. In some embodiments, the treated alkylation feed recovered via processes disclosed herein may include 500 ppm or less nitrogen-containing compounds; 250 ppm or less in other embodiments; 100 ppm or less in other embodiments; 50 ppm or less in yet other embodiments, and 25 ppm or less in yet other embodiments, each on a weight basis. In other embodiments, the treated alkylation feed recovered via processes disclosed herein may include 50 ppm or less nitrites; 25 ppm or less in other embodiments; 10 ppm or less in other embodiments; 5 ppm or less in yet other embodiments, and 2.5 ppm or less in yet other embodiments, each on a weight basis. In some embodiments, the treated alkylation feed recovered via processes disclosed herein may include 0.1 percent or less sulfur; 500 ppm or less in other embodiments; 250 ppm or less in other embodiments; 100 ppm or less in other embodiments; 50 ppm or less in other embodiments; 25 ppm or less in other embodiments; 10 ppm or less in other embodiments; and 5 ppm or less in yet other embodiments, each on a weight basis. In some embodiments, the treated alkylation feed recovered via processes disclosed herein may include 0.1 percent or less oxygenates; 500 ppm or less in other embodiments; 250 ppm or less in other embodiments; 100 ppm or less in other embodiments; 50 ppm or less in other embodiments; 25 ppm or less in other embodiments; 10 ppm or less in other embodiments; and 5 ppm or less in yet other embodiments, each on a weight basis, each on a weight basis. In some embodiments, the treated alkylation feed recovered via processes disclosed herein may include 0.1 percent or less water; 500 ppm or less in other embodiments; 250 ppm or less in other embodiments; 100 ppm or less in other embodiments; 50 ppm or less in other embodiments; 25 ppm or less in other embodiments; 10 ppm or less in other embodiments; and 5 ppm or less in yet other embodiments, each on a weight basis, each on a weight basis. In other embodiments, nitrogen-containing compounds, oxygenates, dienes, and/or sulfur-containing compounds may not be present in the treated alkylation feed at detectable limits.

Referring now to FIG. 1, a simplified process flow diagram of a process for treating an alkylation feedstock according to embodiments disclosed herein is illustrated. In this embodiment, a hydrocarbon stream, fed via flow stream 10 and including olefins, n-alkanes, iso-alkanes, and impurities including one or more of nitrogen-containing compounds and/or oxygenates may be contacted with water, fed via flow stream 12, in water wash column 14. An aqueous fraction, including at least a portion of the nitrogen-containing compounds and/or oxygenates, may be recovered from water wash column 14 via flow line 16. An alkylation feedstock having a reduced oxygen and/or nitrogen content may be recovered from water wash column 14 via flow line 18.

The alkylation feedstock having a reduced nitrogen and/or oxygenate content may include entrained or soluble water, which may be separated from the hydrocarbons by contacting the alkylation feedstock having a reduced nitrogen and/or oxygenate content with an appropriate adsorbent. For example, the alkylate feedstock may be fed via flow line 18 to guard bed 20, containing zeolites or other appropriate absorbents to remove water. Adsorbents in guard bed 20, or other adsorbents in guard beds placed in series with guard bed 20, may also remove acetylenes, dienes, and other components which may result in unwanted poisoning of downstream catalysts or form polymeric materials on the catalyst surface. In some embodiments, two or more guard beds may be placed in parallel or in a lead-lag configuration, allowing for replacement or regeneration of one guard bed while continuing the alkylation/oligomerization feed treatment. If necessary, prior to feeding the alkylation feedstock to adsorber 20, the alkylation feedstock having a reduced nitrogen and/or oxygenate content may be cooled/heated via indirect heat exchange in heat exchanger 22.

Effluent from guard bed 20 may be recovered via flow line 23 and fed to an oligomerization reactor 24 containing an oligomerization catalyst 26. In the oligomerization reactor 24, at least a portion of the olefins may contact the oligomerization catalyst 26, thereby catalytically reacting olefins with themselves to form olefin oligomers. For example, isobutene may be reacted in oligomerization reactor 24 to form isobutene dimers and trimers.

At least a portion of the effluent from the oligomerization reactor 24, including the olefin oligomers, may be fed via flow line 28 to alkylation unit 30. In alkylation unit 30, the olefin oligomers and iso-paraffins, such as contained in the alkylation feedstock or fed separately, may be contacted with sulfuric or hydrofluoric acid fed via flow line 32, thereby reacting the oligomers and iso-paraffins to form an alkylate product. Spent acid may be recovered from alkylation unit 30 via flow line 34. Alkylate product may be recovered via flow line 36 and fed to downstream processes 38, such as gasoline blending, fractionation, or other processes.

Figure 2:
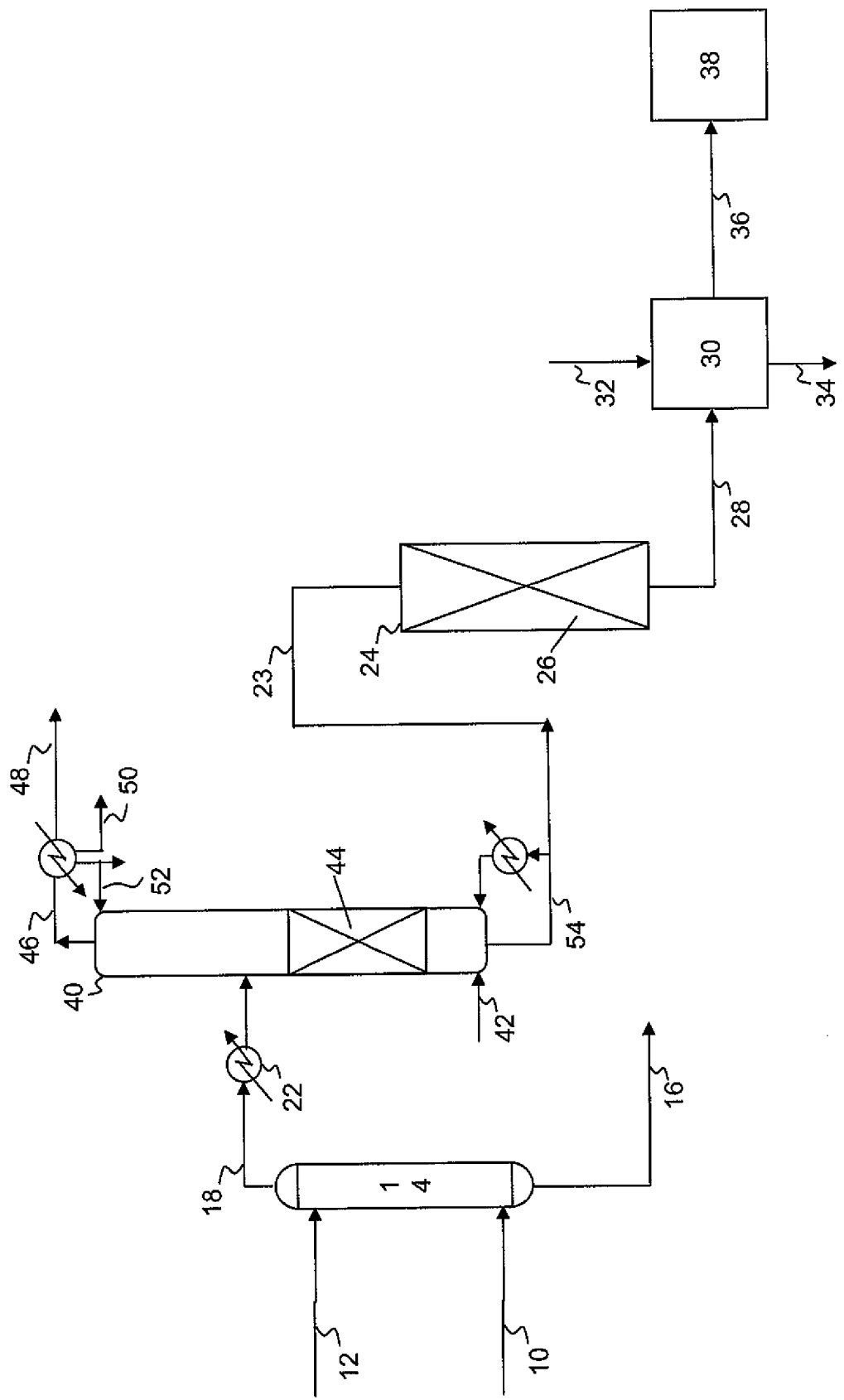
FIG. 2 is a simplified process flow diagram of a process for treating alkylation feedstocks according to embodiments disclosed herein.

Referring now to FIG. 2, where like numerals represent like parts, a simplified process flow diagram of a process for treating an alkylation feedstock according to embodiments disclosed herein is illustrated. In this embodiment, following contact of the alkylate feed in water wash column 14 to remove oxygenates and nitrogen-containing compounds, the alkylate feed may be fed via flow line 18 to catalytic distillation reactor system 40. Hydrogen may also be fed to catalytic distillation reactor system 40 via flow line 42

Catalytic distillation reactor system 40 may include at least one reaction zone 44 containing a hydrogenation catalyst. Concurrently in catalytic distillation reactor system 40, i) the hydrogen and the dienes in the alkylate feedstock may be contacted with the hydrogenation catalyst to selectively hydrogenate at least a portion of the dienes to olefins, and ii) the hydrocarbons may be fractionated from unreacted hydrogen and any water entrained or dissolved in the alkylate feedstock fed via flow line 18.

Water and unreacted hydrogen may be recovered from catalytic distillation reactor system 40 as an overheads fraction via flow line 46. Water and light hydrocarbons may be condensed and separated from the hydrogen, where the hydrogen may be recovered via flow line 48, an aqueous fraction may be recovered via flow line 50, and a hydrocarbon fraction may be recovered via flow line 52, at least a portion of which may be used as column reflux.

A hydrocarbon fraction having a reduced diene content and a reduced nitrogen/oxygenate content may be recovered from catalytic distillation reactor system 40 as a bottoms fraction via flow line 54. At least a portion of the bottoms fraction may then be fed via flow line 23 to oligomerization reactor 24 and processed as described above.

Figure 3:
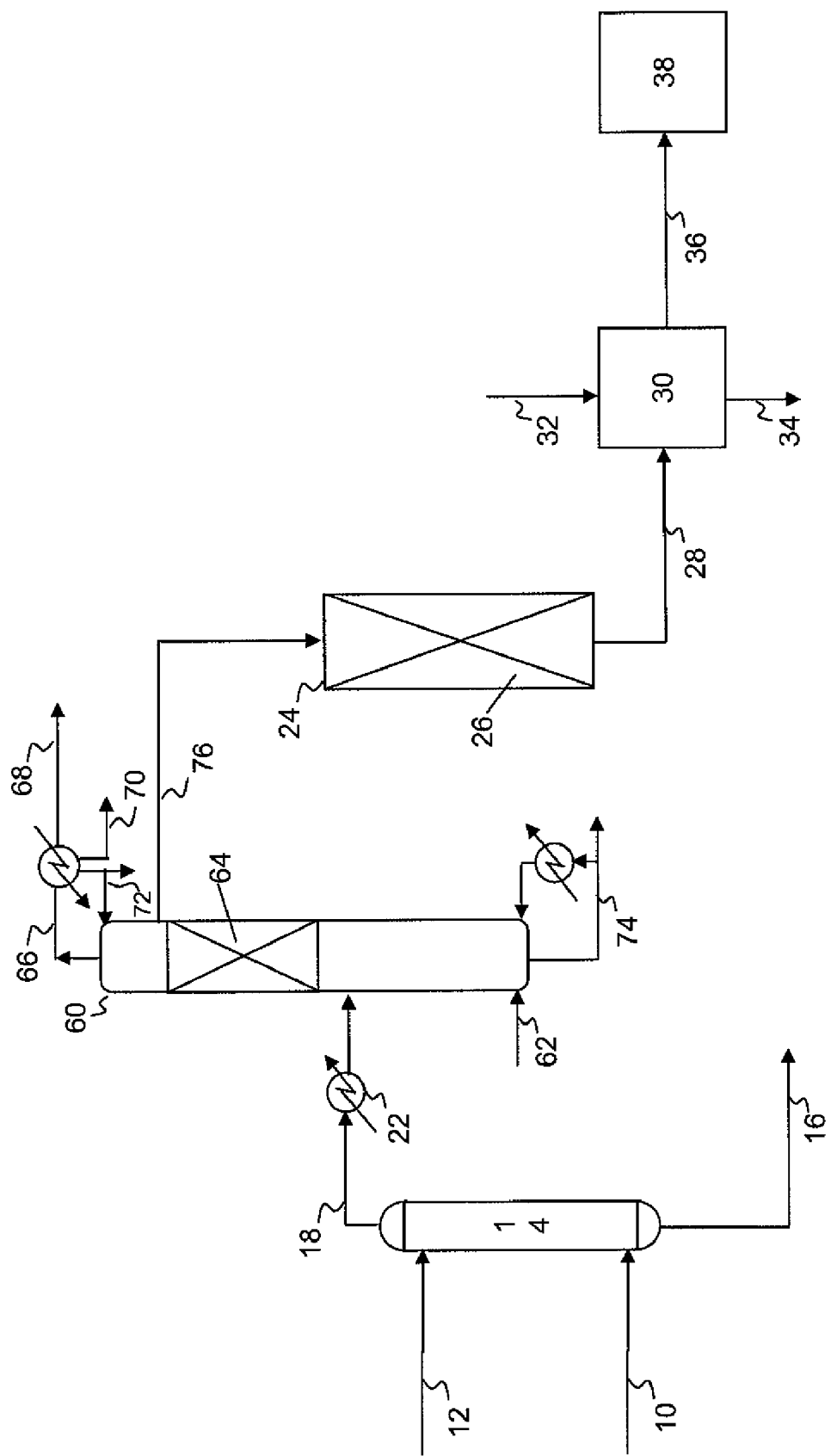
FIG. 3 is a simplified process flow diagram of a process for treating alkylation feedstocks according to embodiments disclosed herein.

Referring now to FIG. 3, where like numerals represent like parts, a simplified process flow diagram of a process for treating an alkylation feedstock according to embodiments disclosed herein is illustrated. In this embodiment, following contact of the alkylate feed in water wash column 14 to remove oxygenates and nitrogen-containing compounds, the alkylate feed may be fed via flow line 18 to catalytic distillation reactor system 60. Hydrogen may also be fed to catalytic distillation reactor system 60 via flow line 62

Catalytic distillation reactor system 60 may include at least one reaction zone 64 containing a hydrogenation catalyst in an upper portion thereof. Concurrently in catalytic distillation reactor system 60, i) the hydrogen and the dienes in the alkylate feedstock may be contacted with the hydrogenation catalyst to selectively hydrogenate at least a portion of the dienes to olefins, and ii) the hydrocarbons may be fractionated from unreacted hydrogen and any water entrained or dissolved in the alkylate feedstock fed via flow line 18.

Water and unreacted hydrogen may be recovered from catalytic distillation reactor system 60 as an overheads fraction via flow line 66. Water and light hydrocarbons may be condensed and separated from the hydrogen, where the hydrogen may be recovered via flow line 68, an aqueous fraction may be recovered via flow line 70, and a hydrocarbon fraction may be recovered via flow line 72, at least a portion of which may be used as column reflux.

A hydrocarbon fraction including heavy sulfides and other compounds boiling in the range of $C_{6+}$ or $C_{7+}$ hydrocarbons may be recovered from catalytic distillation column 60 as a bottoms fraction via flow line 74. A hydrocarbon fraction having a reduced diene content and a reduced nitrogen/oxygenate content may be recovered from catalytic distillation reactor system 60 as a side draw via flow line 76. At least a portion of the side draw may then be fed via flow line 76 to oligomerization reactor 24 and processed as described above.

The side draw may include, for example, a primary $C_4$ cut, a $C_4$ to $C_5$ cut, or a $C_4$ to $C_6$ cut in various embodiments.

In some embodiments, catalyst disposed in reaction zone 44 or a second reaction zone (not shown) within catalytic distillation reactor system 40 may include thioetherification functionality. In these embodiments, in addition to or in lieu of butadiene hydrogenation, dienes and mercaptans may be contacted with the thioetherification catalyst to react at least a portion of the dienes and mercaptans to form heavy sulfides, which may be separated from the desired side draw fraction and recovered along with the bottoms via flow line 74.

Oligomerization, as described above, may be carried out, for example, in a partial liquid phase in the presence of an acid cation resin catalyst, either in straight pass type reaction, such as that disclosed in U.S. Pat. Nos. 4,313,016, 4,540,839, 5,003,124, and 6,335,473, or in a catalytic distillation reaction where there is both a vapor and a liquid phase and a concurrent reaction/fractionation. Iso-olefins that may be oligomerized may include isobutene, isopentenes (isoamylenes), and combinations thereof, which are more reactive than n-olefins, and may be selectively oligomerized.

The primary oligomer products are dimers and trimers of iso-olefins. For example, isobutene may be oligomerized to form a $C_8$ or $C_{12}$ tertiary olefin, isopentene may be oligomerized to form a $C_{10}$ or $C_{15}$ tertiary olefin, and mixtures of isobutene and isopentene may be selectively reacted to form $C_9$, $C_{13}$, and $C_{14}$ tertiary olefins, among other products. During subsequent alkylation, these oligomers react with isoalkane to form alkylate products, such as isooctane, isononane, and isodecane, among others. Instead of the expected reaction between the oligomer and the isoalkane, the oligomer is cracked into its olefin components, that is, the olefins reacted to form the oligomers react with the isoalkane on a molar basis. The result is the same product as alkylation of the mono-olefin alone with the additional benefit of a less exothermic overall alkylation reaction, which may require less refrigeration and a lower energy cost for the alkylation.

Embodiments of the processes described herein may provide for lower overall energy consumption, separating nitrogen-containing compounds, oxygenates, dienes, and sulfur compounds, and oligomerizing a portion of the olefins as a pretreatment to an alkylation feedstock. Advantageously, embodiments disclosed herein may provide for the separation (decrease in concentration or removal) of oligomerization catalyst poisons and acid consuming compounds from alkylation feedstocks.

Advantageously, some embodiments disclosed herein may allow for increased alkylation unit efficiency, resulting from a decreased concentration of inert components. In some embodiments, less acid may be consumed during the alkylation reaction. The increased efficiency may allow for increased reactor throughput for existing alkylation reactors. The increased efficiency may also allow for use of smaller alkylation reactors for newly constructed units.

Additionally, some embodiments disclosed herein may allow for use of existing or stranded equipment. For example, MTBE production columns no longer in service may easily be converted for use in treating the feed according to embodiments disclosed herein.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for treating an alkylation feedstock comprising olefins, n-alkanes, iso-alkanes, and impurities including one or more of butadiene, oxygenates, nitrogen-containing compounds, and sulfur-containing compounds, the process comprising:

contacting an alkylation feedstock containing at least one of oxygenates and nitrogen-containing compounds with water to produce a hydrocarbon fraction having a reduced concentration of the at least one of oxygenates and nitrogen-containing compounds and an aqueous fraction comprising at least a portion of the at least one of oxygenates and nitrogen-containing compounds;

separating water from the hydrocarbon fraction having a reduced concentration to produce a hydrocarbon fraction having a reduced water content;

contacting the hydrocarbon fraction having a reduced water content with an oligomerization catalyst in a first oligomerization reaction zone under oligomerization conditions to react at least a portion of the olefins to form a reactor effluent comprising olefin oligomers; and feeding at least a portion of the reactor effluent to an alkylation unit.

2. The process of claim 1, the process further comprising separating the oligomers from the unreacted iso-olefin, olefins, n-alkanes, and iso-alkanes by fractionation.

3. The process of claim 2, further comprising feeding the separated oligomers as the at least a portion of the reactor effluent fed to the alkylation reactor.

4. The process of claim 2, wherein the contacting to form oligomers and the separating the oligomers are conducted concurrently in a catalytic distillation reactor system.

5. The process of claim 1, wherein the alkylation feedstock comprises at least one of a $C_4$ light cracked naphtha cut, a $C_4$-$C_5$ light cracked naphtha cut, and a $C_4$-$C_6$ light cracked naphtha cut.

6. The process of claim 1, wherein the olefin oligomers comprise dimers and trimers of an iso-olefin.

7. The process of claim 1, wherein the separating comprises contacting the hydrocarbon fraction having a reduced nitrogen concentration with an adsorbent.

8. The process of claim 7, wherein the adsorbent comprises a zeolite.

9. The process of claim 1, wherein the hydrocarbon fraction having a reduced nitrogen concentration further comprises dienes, wherein the separating comprises:

feeding hydrogen and the hydrocarbon fraction having a reduced concentration to a catalytic distillation reactor system comprising at least one reaction zone containing a hydrogenation catalyst formed as a distillation structure;

concurrently in the distillation column reactor system:

i) contacting the hydrogen and the dienes with the hydrogenation catalyst thereby catalytically reacting at least a portion of the dienes and hydrogen to form olefins; and ii) fractionating the resulting hydrocarbons from the water;

recovering the water and unreacted hydrogen as an overheads fraction;

recovering a hydrocarbon fraction having a reduced diene and a reduced water concentration as a bottoms fraction the process further comprising:
feeding the bottoms fraction as the hydrocarbon fraction having a reduced water content to the contacting in a first oligomerization reaction zone.

10. The process of claim 9, wherein the hydrogen is fed to the catalytic distillation reactor system below the at least one reaction zone, and wherein the hydrocarbon fraction having a reduced nitrogen concentration is fed to the catalytic distillation reactor system above the at least one reaction zone.

11. The process of claim 1, wherein the hydrocarbon fraction having a reduced nitrogen concentration further comprises dienes, mercaptans, and other sulfur-containing compounds, wherein the separating comprises:
feeding hydrogen and the hydrocarbon fraction having a reduced concentration to a catalytic distillation reactor system comprising at least one reaction zone containing a hydrogenation catalyst formed as a distillation structure;
concurrently in the distillation column reactor system:
i) contacting the hydrogen and the dienes with the hydrogenation catalyst thereby catalytically reacting at least a portion of the dienes and hydrogen to form olefins; and
ii) fractionating the hydrocarbons from the water;
recovering the water and unreacted hydrogen as an overheads fraction;
recovering a fraction comprising $C_4$ olefins as a side draw;
the process further comprising:
feeding the side draw as the hydrocarbon fraction having a reduced water content to the contacting in a first oligomerization reaction zone.

12. The process of claim 11, further comprising recovering a hydrocarbon fraction comprising at least a portion of the sulfur-containing compounds as a bottoms fraction.

13. The process of claim 11, wherein the hydrogen and the hydrocarbon fraction having a reduced concentration are fed to the catalytic distillation reactor system below the at least one reaction zone.

14. The process of claim 11, wherein the concurrently further comprises contacting the mercaptans and the dienes with a thioetherification catalyst thereby catalytically reacting at least a portion of the dienes and mercaptans to form heavy sulfides.

15. The process of claim 14, wherein the bottoms fraction further comprises the heavy sulfides.

16. A process for treating an alkylation feedstock comprising olefins, n-alkanes, iso-alkanes, and impurities including one or more of butadiene, oxygenates, nitrogen-containing compounds, and sulfur-containing compounds, the process comprising:
contacting the alkylation feedstock with water to produce a hydrocarbon fraction having a reduced concentration of at least one of nitrogen-containing compounds and oxygenates and an aqueous fraction comprising at least a portion of at least one of the nitrogen-containing compounds and the oxygenates;
feeding hydrogen and the hydrocarbon fraction having a reduced concentration to a catalytic distillation reactor system comprising at least one reaction zone containing a hydrogenation catalyst formed as a distillation structure;
concurrently in the distillation column reactor system:
i) contacting the hydrogen and the dienes with the hydrogenation catalyst thereby catalytically reacting at least a portion of the dienes and hydrogen to form olefins; and
ii) fractionating the hydrocarbons from the water;
recovering the water and unreacted hydrogen as an overheads fraction;
recovering a hydrocarbon fraction having a reduced dienes concentration as a bottoms fraction;
contacting the hydrocarbon fraction having a reduced diene content with an oligomerization catalyst in a first oligomerization reaction zone under oligomerization conditions to react at least a portion of the olefins to form a reactor effluent comprising olefin oligomers; and
feeding at least a portion of the reactor effluent to an alkylation unit.

17. A process for treating an alkylation feedstock comprising olefins, n-alkanes, iso-alkanes, and impurities including one or more of butadiene, oxygenates, nitrogen-containing compounds, and sulfur-containing compounds, the process comprising:
contacting the alkylation feedstock with water to produce a hydrocarbon fraction having a reduced concentration of at least one of nitrogen-containing compounds and oxygenates and an aqueous fraction comprising at least a portion of the nitrogen-containing compounds and the oxygenates;
feeding hydrogen and the hydrocarbon fraction having a reduced concentration to a catalytic distillation reactor system comprising at least one reaction zone containing a catalyst formed as a distillation structure;
concurrently in the distillation column reactor system:
i) contacting the hydrogen and the dienes with the catalyst thereby catalytically reacting at least a portion of the dienes and hydrogen to form the corresponding olefins; and
ii) contacting dienes and mercaptans with the catalyst thereby catalytically reacting at least a portion of the dienes and mercaptans to form heavy sulfides;
iii) fractionating the resulting hydrocarbons from the water;
recovering the water and unreacted hydrogen as an overheads fraction;
recovering a hydrocarbon fraction comprising the heavy sulfides and other sulfur-containing compounds as a bottoms fraction; and
recovering a hydrocarbon fraction comprising $C_4$ olefins as a side draw;
contacting the side draw with an oligomerization catalyst in a first oligomerization reaction zone under oligomerization conditions to react at least a portion of the olefins to form a reactor effluent comprising olefin oligomers; and
feeding at least a portion of the reactor effluent to an alkylation unit.

* * * * *